United States Patent
Zinreich et al.

(10) Patent No.: US 8,337,906 B2
(45) Date of Patent: Dec. 25, 2012

(54) NASAL COMPOSITION

(76) Inventors: James Zinreich, Owings Mills, MD (US); Eva Zinreich, Owings Mills, MD (US); Helen Zinreich Shafer, Owings Mills, MD (US)

(*) Notice: Subject to any disclaimer, the term of this patent is extended or adjusted under 35 U.S.C. 154(b) by 64 days.

(21) Appl. No.: 12/885,715

(22) Filed: Sep. 20, 2010

(65) Prior Publication Data

US 2011/0086114 A1    Apr. 14, 2011

Related U.S. Application Data

(63) Continuation-in-part of application No. 11/782,959, filed on Jul. 25, 2007, now abandoned.

(60) Provisional application No. 60/820,289, filed on Jul. 25, 2006.

(51) Int. Cl.
A61K 33/14    (2006.01)
A61K 31/375   (2006.01)
A01N 59/08    (2006.01)

(52) U.S. Cl. ........................................ 424/680; 514/474

(58) Field of Classification Search ................... None
See application file for complete search history.

(56) References Cited

U.S. PATENT DOCUMENTS

| | | | |
|---|---|---|---|
| 4,826,683 A * | 5/1989 | Bates ........................... | 424/641 |
| 4,885,305 A | 12/1989 | Kiechel et al. | |
| 5,169,849 A | 12/1992 | Kiechel et al. | |
| 5,376,365 A | 12/1994 | Dikstein | |
| 5,508,282 A * | 4/1996 | Tulin-Silver et al. ..... | 514/263.31 |
| 5,603,935 A | 2/1997 | Jian et al. | |
| 5,688,532 A | 11/1997 | Bryce-Smith | |
| 5,897,872 A | 4/1999 | Picciano | |
| 5,898,037 A | 4/1999 | Marx | |
| 6,171,611 B1 | 1/2001 | Picciano | |
| 6,180,663 B1 | 1/2001 | Lang | |
| 6,258,372 B1 | 7/2001 | Jones | |
| 6,344,210 B2 | 2/2002 | Fust | |
| 6,528,081 B1 | 3/2003 | Zellner | |
| 6,596,284 B1 | 7/2003 | Fleming | |
| 6,641,799 B2 | 11/2003 | Goldberg | |
| 2003/0059440 A1 | 3/2003 | Clarot et al. | |
| 2003/0111491 A1 | 6/2003 | Mehta | |
| 2005/0084454 A1 | 4/2005 | Fust | |
| 2005/0202097 A1 | 9/2005 | Maskin | |
| 2005/0220719 A1 | 10/2005 | Salman | |

OTHER PUBLICATIONS

Min et al. (Abstrct of: Otoloaryngol Head neck Surg 2001, 124(3): 313-316) 1 page.*
Beck, Drug Reference for EMS Providers, 2002, pp. 724-725.

* cited by examiner

*Primary Examiner* — Ernst Arnold
(74) *Attorney, Agent, or Firm* — Hahn Loeser & Parks, LLP; Keith J. Marcinowski

(57) ABSTRACT

A nasal spray solution for use as a nasal spray and methods of using the solution are disclosed. The nasal spray solution moisturizes nasal passages and alleviates nasal dryness. The solution includes a hypotonic saline solution, wherein the saline solution is hypotonic with respect to cells of the nasal mucosa of the nasal passages, a buffering agent, a lubricating agent, and an anti-microbial agent.

12 Claims, 1 Drawing Sheet

NASAL COMPOSITION

Figure 1:
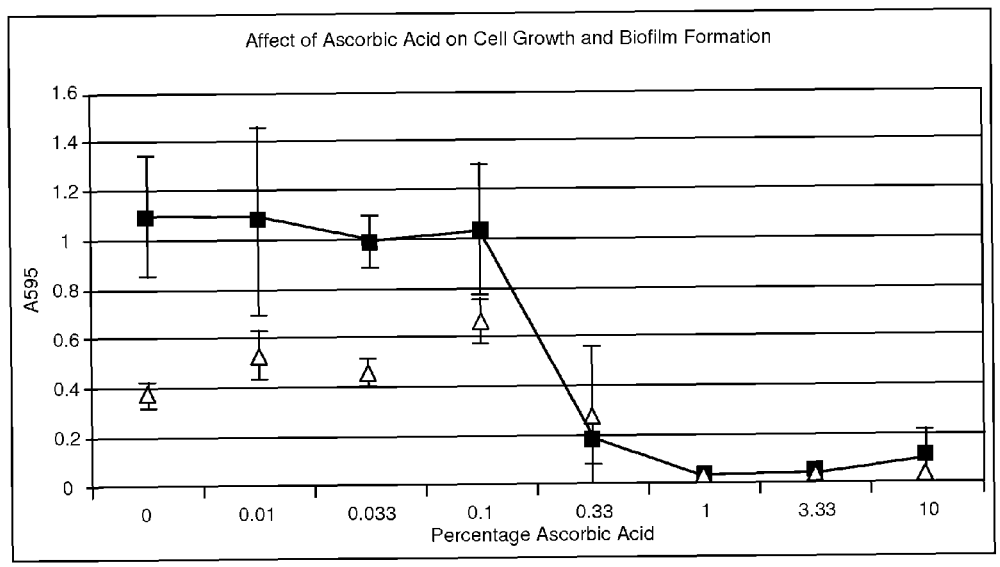

This application is a continuation-in-part of U.S. application Ser. No. 11/782,959 filed Jul. 25, 2007, which claims priority to U.S. Provisional Application Ser. No. 60/820,289, filed Jul. 25, 2006, and is hereby incorporated by reference.

TECHNICAL FIELD

The invention relates to a saline solution for a nasal spray that moisturizes nasal passages and alleviates nasal dryness and methods of use. In particular, the invention relates to a hypotonic or isotonic saline solution for a nasal spray, which includes a lubricating agent and an anti-microbial agent that moisturizes nasal passages and lessens or alleviates nasal dryness.

BACKGROUND OF THE INVENTION

The nose is a complicated structure that serves dual functions as the organ for the sense of smell and as an entry to the respiratory tract. As part of the respiratory tract, a healthy nose moisturizes and warms incoming air and filters out foreign materials.

Nasal passages and other portions of the respiratory tract are lined with specialized tissue layers. In the nose and sinus areas this tissue is often called the nasal mucosa. Like many tissues, the nasal mucosa is composed of several cell layers and cell types. Mucous cells are one type of cell found in the nasal mucosa. These cells are found throughout the nasal mucosa and are generally clustered into small glands. These glands secrete a sticky substance called mucus. Mucus is composed of water, shed epithelial (surface) cells, dead leukocytes, mucin, and inorganic salts, among other things, that are all held in suspension. Mucus functions as a trap for airborne particles (e.g., dust, bacteria, and viruses) that enter the nasal passages. Mucus also lubricates the walls of the nose, sinuses, and throat.

In a healthy nose, the mucus is cleared from the nasal passages on a regular basis by a layer of cells in the nasal mucosa called the ciliated columnar epithelium. These cells possess small hair-like projections called cilia that undulate and "sweep" mucus through the nasal passages allowing it to drain to the back of the throat where it can be swallowed or expelled. This line of defense protects the body against the bacteria and viruses that continually enter the nose and mouth.

Connected to the nose are sinuses or air-filled cavities located behind certain facial bones. There are four groups of sinuses, namely, frontal, sphenoidal, ethmoidal, and maxillary. The sinuses are also lined with mucus secreting tissue. The sinuses are normally kept clear when mucus drains through them into the nasal passages. However, under low humidity atmospheric conditions typically found on airplanes and in desert areas, the sinuses can become dry resulting in nasal discomfort.

Nasal sprays have been commercially available for moisturization of the nasal membranes. Such sprays normally are water containing surfactants to spread the water over the nasal membranes and enhance the penetration of the water into the surface layers of the membranes. There is no therapeutic function of the water penetration.

Therefore, it would be advantageous to provide a hypotonic or isotonic saline solution for a nasal spray or nasal drop solution that includes a lubricating agent and an anti-microbial agent for moisturizing the nasal passages and lessening or alleviating nasal dryness.

SUMMARY OF THE INVENTION

An embodiment of the invention is directed to a solution for a nasal spray or nasal drops that moisturize the nasal passages and lessens or alleviates nasal dryness. The solution includes a hypotonic saline solution, wherein the saline solution is hypotonic with respect to cells of the nasal mucosa of the nasal passages, a buffering agent, a lubricating agent, and ascorbic acid provided in a range from about 0.25% to about 1.00% by volume of the composition of the nasal spray solution, wherein the ascorbic acid is an anti-microbial agent and a mucolytic agent, wherein the ascorbic acid increases cilia beat frequency which provides enhanced mucous transport in the nasal passages.

Another embodiment of the invention is directed to a method of moisturizing nasal passages and alleviating nasal dryness. The method includes the steps of providing a nasal spray solution, the solution comprising a hypotonic saline solution, wherein the saline solution is hypotonic with respect to cells of the nasal mucosa of the nasal passages and ascorbic acid provided in a range from about 0.25% to about 1.00% by volume of the composition of the nasal spray solution, and wherein the ascorbic acid is a mucolytic agent that increases cilia beat frequency which provides enhanced mucous transport in the nasal passages, and delivering at least one application of the solution into at least one nostril, wherein the solution moisturizes the nasal mucous membrane of the nasal passages. The method further includes a buffering agent and a lubricating agent.

In yet a further embodiment of the invention, a nasal spray solution for moisturizing nasal passages and alleviating nasal dryness is disclosed. The solution includes a hypotonic saline solution, wherein the saline solution is in a range from about 0.4% to about 0.6% by weight sodium chloride and hypotonic with respect to cells of the nasal mucosa of the nasal passages, a buffering agent, a lubricating agent, wherein the lubricating agent is in a range from about 0.5% to about 1.0% by volume of the composition of the solution, and ascorbic acid provided in a range from about 0.25% to about 0.50% by volume of the composition of the nasal spray solution, wherein the ascorbic acid is an anti-microbial agent and a mucolytic agent, wherein the ascorbic acid increases cilia beat frequency which provides enhanced mucous transport in the nasal passages.

This and other objects of the invention are achieved by the hypotonic or isotonic saline solution found in the spray liquid for the nasal spray used for moisturizing the nasal passages to alleviate nasal dryness, as described in more detail below.

DETAILED DESCRIPTION OF THE DRAWINGS

Figure 2:
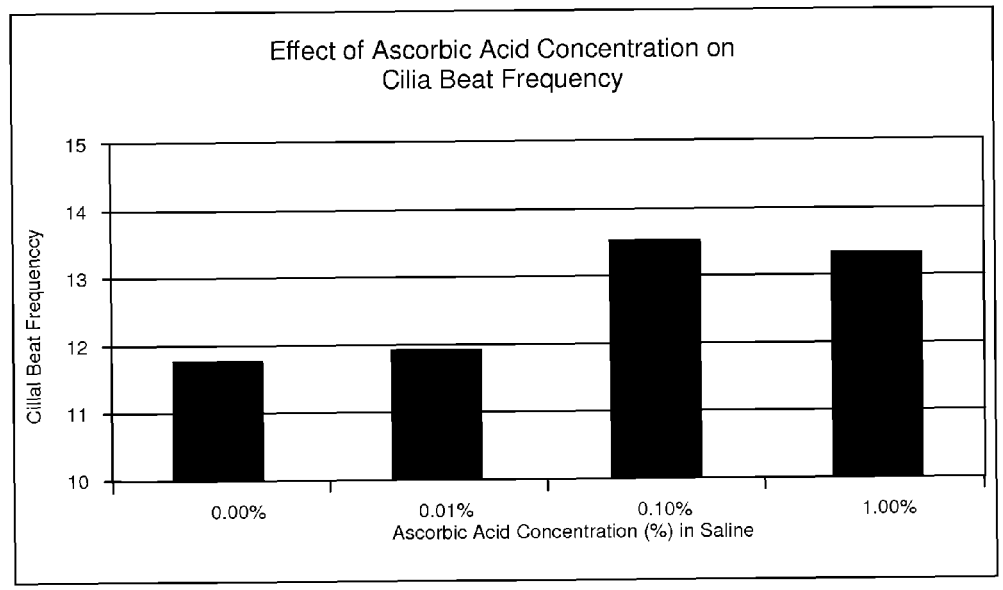

FIG. 1 is a graph detailing the effect of different concentrations of ascorbic acid on cell growth and biofilm formation; and FIG. 2 is a graph detailing the effect of different concentrations of ascorbic acid on cilia beat frequency.

DETAILED DESCRIPTION OF THE INVENTION

In general, a solution for a nasal spray that moisturizes and provides anti-microbial activity towards airborne diseases when applied into nasal passages is disclosed. The solution is a hypotonic or isotonic nasal spray or nasal drops that aid in the moisturizing, in offering some localized anti-microbial activity and increased ciliary function.

For purposes of this discussion, osmosis may be defined as the spontaneous passage or diffusion of water through a semipermeable membrane which is a membrane that is capable of blocking the passage of dissolved substances from an area of higher water concentration to an area of lower water concentration. Stated alternatively, water will diffuse upwardly towards its concentration gradient or into a hypotonic environment to achieve a state of equilibrium. In an isotonic environment, water will essentially be maintained in its environment since a state of equilibrium has been achieved. The semipermeable membranes at issue here are the tissues of the nasal mucosa and even the plasma membranes of individual cells within the tissues.

In an embodiment of the invention, the solution for a nasal spray is a hypotonic or isotonic saline solution. In particular, the saline solution is hypotonic with respect to the tissue and cells of the nasal mucosa. A hypotonic solution has less than an amount of dissolved solute in it when compared to its surroundings and an isotonic solution has about an equal amount of dissolved solute in it when compared to its surroundings. Accordingly, in one embodiment of the invention, the saline solution is equal to or less than about 0.9% by weight (i.e., equal to or less than about 9.0 mg/ml) salt in an aqueous solution. In one embodiment, the saline solution is in a range from about 0.4% to about 0.6% by weight of sodium chloride or sodium chloride equivalent in water (i.e. in the range from about 4.0 mg/ml to about 6.0 mg/ml).

As noted above, the composition according to the invention uses osmosis, with the use of the hypotonic or isotonic saline solution, to aid in the physiological increase of ciliary action by way of increasing the mucociliary clearance in the nasal passages. In general terms with the hypotonic saline solution, the osmotic effect utilized in the invention can be described as follows: by bathing the nasal mucosa in a hypotonic solution, osmotic forces will drive or pull water into the free spaces in the nasal mucosa tissue and into the intracellular environment from the nasal passages thereby hydrating the nasal mucosa, thus providing a moisturizing effect. Furthermore, in general terms with the isotonic saline solution, the osmotic effect utilized in the invention can be described as follows: by bathing the nasal mucosa in an isotonic solution, osmotic forces, since the concentration of the solute in the solution is substantially the same as the concentration in the environment, will essentially allow water to diffuse between and into the free spaces in the nasal mucosa tissue and the intracellular environment from the nasal passages thereby hydrating the nasal mucosa, thus providing a moisturizing effect. The part of the hypotonic or isotonic solution not participating in the osmotic effect, primarily water, will further moisturize the nasal passages and provide an increase in mucociliary clearance of the mucus from the nasal passages.

This osmotic effect requires that the composition be hypotonic or isotonic with respect to the nasal mucosa. Although some of the components in the composition contribute to the hypotonicity or isotonicity of the composition, as used herein, the term osmotic agent refers to an agent specifically added to the composition to decrease the solute level in the composition and contribute to achieving hypotonicity of the spray liquid or nasal drops. In an embodiment of the invention, the osmotic agent used in the practice of the invention is the saline solution previously described.

Besides water, the spray liquid can also include pharmaceutically acceptable additives. The additives, as used herein, include pharmaceutically acceptable carriers, excipients, buffering agents or stabilizers which are nontoxic to the cell or mammal being exposed thereto at the dosages and concentrations employed. Often the pharmaceutically acceptable additive is an aqueous pH buffered solution. Examples of physiologically acceptable carriers include buffers such as, but not limited to, phosphate, borate, citrate and other organic acids; carbohydrates including glucose, mannose, or dextrins; chelating agents such as EDTA; and sugar alcohols such as mannitol.

In yet another embodiment of the invention, the solution of the nasal spray contains an effective amount of an anti-microbial, for example vitamin C or ascorbic acid, to provide an increased localized antibacterial effect. The vitamin C is present in a concentration from about 0.25% to about 1.00% by volume. It has also been determined that the ascorbic acid may also act as a mucolytic agent through an increase in the beating rate of the cilia. In this capacity, the mucolytic agent performs as a mucociliary stimulant that assists in and increases the breakup and clearance of mucous. The action of cilia in cells of the nasal mucosa is important in keeping the nasal passages clear of mucus. If cilia function is subnormal, mucus will build up and contribute to congestion of the nasal passages.

A preservative may also be optionally used to maintain the integrity of the composition. Suitable preservatives are well known to those skilled in the art and include sorbates, benzoates and mixtures thereof. However, a small quantity (e.g., less than 1% by volume) of potassium sorbate, potassium benzoate or mixtures thereof may be added to the composition.

In a further embodiment of the invention, the liquid spray is a hypotonic or isotonic composition for the use in osmotic moisturization and mucociliary clearance in the nasal passages. The composition is a hypotonic or isotonic saline solution that includes water, sodium chloride, equal to or less than about 0.9% by weight, vitamin C, in the range from about 0.25% to about 1.00% by volume, and glycerol, alone or in combination with sorbitol, in the range from about 0.5% to about 1.0% by volume. In one embodiment, the liquid spray is pH buffered with the addition of mono- and/or di-basic sodium phosphate buffers until a desired physiological pH is achieved.

The nasal spray of the invention is used to moisten the nasal passages in order to alleviate nasal dryness, provide antimicrobial activity and increase mucociliary clearance. Under these circumstances, at least one spray application per nostril will clean and moisturize the nasal mucous membrane. This accomplishes an improved nasal comfortness and well-being by providing a lasting preventative care with respect to illnesses of the respiratory tracts.

EXPERIMENTAL

Anti-Bacterial Effect of Ascorbic Acid

The anti-bacterial properties of ascorbic acid were evaluated by testing the effect of dilutions of the material on both biofilm and planktonic growth forms of a *Pseudomonas aeruginosa* isolate that was obtained from patients with cystic fibrosis. *Pseudomonas aeruginosa* is a common pathogen isolated from the sinuses of patients with chronic rhinosinusitis. The results of this evaluation as shown graphically in FIG. 1.

Known concentrations of the bacteria were placed in the 96 well culture plates. Dilutions of ascorbic acid (0% (Control), 0.010%, 0.033%, 0.100%, 0.330%, 1.000%, 3.330%, and 10.000%) were added to predetermined wells. A lid with 96 pegs was placed on the plate to facilitate biofilm formation and removal. After incubation, the lids with the pegs were separated from the base wells. The bacterial growth was measured both on the pegs as a biofilm and in the wells as planktonic cells. Anti-bacterial activity is demonstrated in the following graph as a dose dependent inhibition of both planktonic and biofilm forms of *Pseudomonas aeruginosa*.

More specifically, both bacterial planktonic and biofilm growth were determined using a modification of the plate based assay described by "Moskowitz et al. (Moskowitz S M, Foster J M, Emerson J, et al. Clinically feasible biofilm susceptibility for isolates of *Pseudomonas aeruginosa* from patients with cystic fibrosis. J. Clin. Microbiol. 2004, 42: 1915-1922). Briefly, *Pseudomonas aeruginosa* (PAO1) cultures were grown to log phase ($OD_{600}$=0.5) and 150 µl of culture was placed in 96 well flat bottom plates (Nalgene Nunc International, Rochester, N.Y.). A lid containing 96 polystyrene pegs (Nunc, TSP 96 well microtiter plate lid) was placed on top and the pegs are suspended in the wells. The lid was loosely fixed to the plate using a strip of parafilm (Menasha, Wis.). The plate was incubated without shaking at 37° C. for 20 hours at which time the lid containing the pegs were carefully removed from the 96 well culture plate and rinsed 3 times in sterile water. The original culture plate was read at $OD_{600}$ to determine planktonic growth. The pegs were placed in another 96 well plate containing Gram Crystal Violet (CV) (20 g/L CV, 8 g/L ammonium oxalate, 2% ethanol) for 15 minutes and then rinsed in sterile water three times to remove unbound crystal violet. The pegs were then immersed in a 96 well plate containing 200 µl of 100% ethanol for 15 minutes. The lid containing the pegs was then removed from the eluted crystal violet and read at 595 nm using a plate reader (Microplate Reader 680, Bio-Rad Hercules, Calif.). In order to determine the anti-bacterial activity of the nasal spray solution, four dilutions, as previously described, were added to the initial bacterial culture prior to the 20 hour incubation. Antibacterial activity was determined by a dose dependent inhibition of planktonic growth as well as biofilm formation.

As seen in FIG. 1, the y-axis represents absorption at 595 nm, which is one method of assessing bacterial concentration in solution. Additionally, using a crystal violet staining assay for biofilms we can quantify biofilm formation, wherein peak absorbance for crystal violet is~600 nm. Thus, the semi-log dose response curve demonstrates that the addition of ascorbate between 0.1% and 1% to the bacterial broth inhibits both pseudomonal planktonic growth as well as biofilm formation.

Effect of Ascorbic Acid on Cilia Beat Frequency (CBF)

Human sinusoidal samples were subjected to concentrations of the nasal spray solution to test the effect of the product on the cilia beat frequency (CBF). The samples were microscopically visualized and the images captured at a rate of 250 frames per second using digital image sampling. The samples were first visualized for two to three seconds every minute for five minutes to establish a baseline Cilia Beating Rate. The samples were then subjected to dilutions of the formulation and the effect on the beating rate was measured by comparing this rate to the baseline rate. The results of the measured CBF are seen in FIG. 2.

More specifically, using a dual temperature controlled perfusion chamber, differential interference contrast microscopy, and high speed digital video, epithelial ciliary function was analyzed as described previously (Schipor I, Palmer I N, Cohen A S, Cohen N A. Quantification of ciliary beat frequency in sinonasal epithelial cells using differential interference contrast microscopy and high speed digital video imaging. Am J Rhino 12006; 20: 124-7). Residual human sinonasal mucosa from surgery was placed in ice cold Locke Ringer's solution [136 mM Nacl, 5.6 mM KCI, 10 mM HEPES, 14.3 mM NaHCO, 1.2 mM $MgCl_2$, 2.2 mM $CaCl_2$ and 11.5 mM dextrose, pH 7.35] for transport. Explants were placed in a glass perfusion chamber on a thermostatically controlled stage and held in place with a nylon grid (1.5 mm) whose outer frame is snapped into the inside of the perfusion chamber. The stage and perfusate were maintained at a temperature between 35.5° C. and 37° C. with a dual channel heater (Warner Inst., Hamden Conn.). The perfusion chamber (Warner Inst) provided superfusion (1-2 ml/min.) of the tissue with Locke Ringer's solution via a gravity-flow system.

Images were visualized using a Leica DMLFSA microscope set on an air table (TMC, Peabody, Mass.) using a water immersion 63× objective and differential interference contrast (DIC) optics (Leica Microsystems, Inc., Bannockburn, Ill.). Images were captured by a Model 500 Redlake MotionPro high speed monochrome digital video camera (DEL Imaging Systems, LLC, Cheshire, Conn.). The digital image-sampling rate is set at 250 frames per second (fps) with a resolution of 1280×1024 pixels. A two to three second video was recorded every minute for 5 minutes to establish a baseline frequency. The perfusate was then rapidly switched to the nasal spray solution. The video images were written to a PCI 2.2 board and then analyzed using Midas Professional Analyst video imaging processing software (XCitex, Cambridge, Mass.).

Beating cilia were analyzed using the 1-D line tracking algorithm included in the motion analysis software. After locating a region of beating cilia, an analysis grid was created by drawing a line across a segment of beating cilia. The software captured the motion history within the analysis grid for the duration of the video and recorded the gray scale intensity variation as a function of time. This track history represented the oscillations of the cilia in the form of a time-based waveform graph. The frequency was calculated as the inverse of the peak-to-peak distance of this waveform. For each sample, at least three areas of beating cilia within the same field were analyzed and the reported frequencies represent the arithmetic means of these values. This was repeated in triplicate for four dilutions including the stock, 10% stock, and 1% stock, and 0.1% stock.

Analysis of the results demonstrated an increasing trend of sinonasal CBF with increasing concentration of ascorbate (0.01% to 0.1%). Mathematical modeling demonstrated that the energy transferred by cilia to the mucus blanket is proportional to the square of the CBF [Silberberg, A. On mucociliary transport. Biorheology 27, 295-307 (1990)]. Additionally, the experimental data demonstrated that a relatively modest increase in CBF (16%) results in a large increase (56%) in surface liquid velocity, i.e., mucociliary transport [Seybold, Z. V. et al. Mucociliary interaction in vitro: effects of physiological and inflammatory stimuli. J Appl Physiol 68, 1421-6 (1990)]. Thus a change from 11.8 Hz (control) to 1304 Hz (0.1% ascorbate) represents a 13.5% increase in CBF, but represents approximately a 50% increase in mucous transport.

Based on the foregoing disclosure, it should be apparent that the liquid spray for a nasal spray of the invention will achieve the objectives set forth above. It is therefore understood that any evident variations will fall within the scope of the claimed invention. Thus, alternate specific component elements can be selected without departing from the spirit of the invention disclosed and described herein.

What is claimed is:
1. A nasal spray solution for moisturizing nasal passages and alleviating nasal dryness, the solution consisting of:
   a hypotonic saline solution, wherein the saline solution is hypotonic with respect to cells of the nasal mucosa of the nasal passages;
   a buffering agent;
   a lubricating agent; and
   ascorbic acid, wherein the ascorbic acid increases the cilia beat frequency by at least 10% which provides an increase in mucous transport of about 50% in the nasal passages and reduces biofilm formation.

2. The solution of claim 1, wherein the saline solution is less than 0.9% by weight sodium chloride.

3. The solution of claim 2, wherein the range of sodium chloride is in a range from about 0.4% to about 0.6% by weight.

4. The solution of claim 1, wherein where the lubricating agent is glycerol, sorbitol or mixtures thereof.

5. The solution of claim 1, wherein the lubricating agent is present in a range from about 0.5% to about 1.0% by volume of the composition of the solution.

6. A nasal spray solution for moisturizing nasal passages and alleviating nasal dryness, the solution consisting of:
   a hypotonic saline solution, wherein the saline solution is in a range from about 0.4% to about 0.6% by weight sodium chloride and hypotonic with respect to cells of the nasal mucosa of the nasal passages;
   a buffering agent;
   a lubricating agent, wherein the lubricating agent is in a range from about 0.5% to about 1.0% by volume of the composition of the solution; and
   ascorbic acid wherein the ascorbic acid increases the cilia beat frequency by at least 10% which provides an increase in mucous transport of about 50% in the nasal passages and reduces biofilm formation.

7. A method of moisturizing nasal passages and alleviating nasal dryness, the method comprising the steps of:
   providing the nasal spray solution of claim 1; and
   delivering at least one application of the solution into at least one nostril, wherein the solution moisturizes the nasal mucous membrane of the nasal passages.

8. The method of claim 7, wherein the at least one application is sprayed into the at least one nostril.

9. The method of claim 7, wherein the saline solution is less than about 0.9% by weight sodium chloride.

10. The method of claim 9, wherein the range of sodium chloride is in a range from about 0.4% to about 0.6% by weight.

11. The method of claim 7, wherein where the lubricating agent is glycerol, sorbitol or mixtures thereof.

12. The method of claim 11, wherein the lubricating agent is in a range from about 0.5% to about 1.0% by volume of the composition of the solution.

\* \* \* \* \*